(12) United States Patent
Yaguchi

(10) Patent No.: US 8,038,684 B2
(45) Date of Patent: Oct. 18, 2011

(54) INTRAOCULAR DEVICE FOR RETAINING A LENS CAPSULE

(75) Inventor: Shigeo Yaguchi, Yokahoma (JP)

(73) Assignee: Showa University, Tokyo (JP)

( * ) Notice: Subject to any disclaimer, the term of this patent is extended or adjusted under 35 U.S.C. 154(b) by 1506 days.

(21) Appl. No.: 10/748,234

(22) Filed: Dec. 31, 2003

(65) Prior Publication Data
US 2004/0230203 A1 Nov. 18, 2004

(30) Foreign Application Priority Data

May 15, 2003 (JP) .................................. 2003-172646

(51) Int. Cl.
*A61F 9/00* (2006.01)
*A61M 5/00* (2006.01)
(52) U.S. Cl. ........................................ 606/107; 600/236
(58) Field of Classification Search .................. 600/206, 600/227, 236, 201, 208, 209, 235; 604/8; 606/107
See application file for complete search history.

(56) References Cited

U.S. PATENT DOCUMENTS

| | | | |
|---|---|---|---|
| 3,656,481 A | 4/1972 | Ness | |
| 5,242,450 A | 9/1993 | McDonald | |
| 5,290,292 A * | 3/1994 | Householder | ............... 606/107 |
| 5,376,099 A | 12/1994 | Ellis et al. | |
| 5,407,441 A | 4/1995 | Greenbaum | |
| 5,514,076 A * | 5/1996 | Ley | ............... 600/206 |
| 5,716,328 A * | 2/1998 | Grieshaber et al. | ............... 600/206 |
| 5,807,244 A * | 9/1998 | Barot | ............... 600/236 |
| 5,843,184 A | 12/1998 | Cionni | |
| 6,183,480 B1 | 2/2001 | Mackool | |
| 6,231,583 B1 | 5/2001 | Lee | |
| 6,560,916 B1 * | 5/2003 | Maxim | ............... 43/43.16 |
| 6,752,086 B2 | 6/2004 | Kravel et al. | |
| 2002/0055753 A1 | 5/2002 | Silvestrini | |
| 2003/0007925 A1 | 1/2003 | Khan et al. | |

FOREIGN PATENT DOCUMENTS

| | | |
|---|---|---|
| JP | 10-80441 | 3/1998 |
| JP | 10-80441 | 10/2001 |
| JP | 2002-95691 | 4/2002 |

OTHER PUBLICATIONS

Japanese Office Action mailed Apr. 18, 2006 in corresponding Japanese Patent Application No. 2003-172646.
Japanese Office Action mailed Aug. 22, 2006 in corresponding Japanese Patent Application No. 2003-172646.
"Capsular stabilization device to preserve lens capsule integrity during phacoemulsification with a weak zonule", Nishimura et al., J. Cataract Refract Surgery, 2006, 32:392-395.

(Continued)

*Primary Examiner* — Vy Q Bui
(74) *Attorney, Agent, or Firm* — Staas & Halsey LLP

(57) ABSTRACT

A rod-shaped device holds the equatorial region of the lens capsule during cataract/intraocular lens implantation surgery of patients with a weak or ruptured Zinn zonule. The device has a handle with a length of 6 mm or more and a thickness ranging from 0.01 mm to 1.0 mm, a tip bent into an acute angle, with the length up to this angled tip being 1.5 mm or more from the trough of the bend, and the bent tip having a linear branched or flat pad, with the width between the branches being 1 mm or more or the flat pad having a surface area of 1 mm$^2$ or more.

8 Claims, 2 Drawing Sheets

OTHER PUBLICATIONS

Merriam Webster's Collegiate Dictionary, Tenth Ed., p. 126, definition of "blunt".
"Surgical Instruments 101, An Introduction to KMedic Certified Instruments" by Kapcyznski, 1997, 15 pp.
"The History and Evolution of Surgical Instruments, IX, Scissors and Related Pivot-Controlled Cutting Instruments," by Kirkup, Royal College of Surgeons of England, Ann R. Coll Surg. Engl 1998, 80: 422-432.
*Combined Tactical Systems, Inc.* v. *Defense Tech. Corp. of America,* Southern Dist. Court of New York, Opinion dated Apr. 4, 2006.
Decision on Appeal, Ex Parte Khan, PTO Bd. Of Appeals and Interferences, Appeal No. 2007-2211, dated Jan. 30, 2008.

* cited by examiner

INTRAOCULAR DEVICE FOR RETAINING A LENS CAPSULE

This application claims the benefit under 35 U.S.C. Section 119 of Japanese Application No. 2003-172646, filed May 15, 2003, which his hereby incorporated by reference in its entirety into this application.

BACKGROUND OF THE INVENTION

1. Field of the Invention

The present invention is related to eye surgery and, more particularly, to a device and method for retaining a lens capsule during ophthalmologic surgery, particularly cataract surgery and intraocular lens implantation surgery.

2. Description of the Related Art

In the field of ophthalmology, cataract surgery and intraocular lens implantation surgery are now common, with high surgical success rates and improved rates of postoperative recovery of the patient's visual functions. In cataracts, the intraocular lens becomes clouded, causing impairment of visual acuity, and the most widely used technique for treatment of this symptom is phacoemulsification/aspiration surgery.

In this surgical technique, the anterior capsule of the lens, which is a clear membrane enclosing the surface of the lens, is incised using an incision needle (anterior capsulotomy). Next, a phacoemulsification/aspiration needle is inserted into the eye via the incision wound in the corneal limbus, and the lens cortex and nucleus are emulsified and aspirated out via the site of the anterior capsulotomy. Finally, an intraocular lens is implanted in the bag-shaped lens capsule. Accordingly, it is vitally important in these phacoemulsification/aspiration and intraocular lens implantation procedures to maintain the intracular lens capsule, which holds the intraocular lens in position, in a round bag shape.

The lens is connected to a transparent tissue composed of countless thin fibers referred to as the Zinn zonule which runs from near the equatorial region of the lens capsule to the ciliary body, and this maintains the lens' shape and position. During surgery, the lens is subjected to external pushing and pulling forces in response to movement of a retractor and the phacoemulsification/aspiration needle. The Zinn zonule is also subjected to stress accompanying this movement of the lens, but this usually does not result in damage to the Zinn zonule because the healthy zonule is ordinarily sufficiently strong.

However, in elderly patients, patients with poor pupil dilation, patients with pseudoexfoliation syndrome, etc., it is frequently the case that the Zinn zonule is inherently weak, partially torn or out of position. In such patients, there is an increased risk of complications such as luxation of the lens if the zonule ruptures or the extent of this rupture expands, or dislocation of the luxated lens into the vitreous cavity.

U.S. Pat. No. 6,183,480 of Mackool describes a device for stabilizing the lens capsule. Mackool's device is a hook-shaped lens capsule stabilizer in which the margin of anterior capsulotomy with a brittle or ruptured Zinn zonule is subjected to traction together with the ring of the iris. Mackool's device has a hook-shaped, curved portion which catches and pulls on the margin of the capsulotomy to retract same, but it cannot be used in situations where the incised anterior capsule shows fissures. Cases of a brittle or ruptured Zinn zonule are treated as refractory cases of cataract surgery, and it is known that in such cases, extraction of the lens nucleus is difficult, and complications such as lens dislocation, posterior capsule rupture, intraocular lens displacement, and dislocation into the vitreous cavity may occur.

Maintenance of favorable dilation status is one of the conditions for safely performing cataract surgery. Eye drops are ordinarily used to dilate the pupil, but some patients with a history of conditions such as glaucoma or uveitis fail to respond to eye drops, making it impossible to sufficiently dilate the pupil.

In such poorly dilated eyes, a surgical auxiliary device referred to as an iris retractor has conventionally been used in order to forcibly dilate the pupil. When a metal iris retractor is used in patients with a brittle or ruptured Zinn zonule, the edge of the iris (papillary margin) and the margin of anterior capsulotomy are pulled together, subjecting the lens capsule to traction as well, but it is impossible to secure the proper shape of the lens capsule as the retraction site is a margin of the capsulotomy only.

In the lens capsule-stabilizing device developed by Mackool, the retraction site also is a margin of the capsulotomy only, making it impossible to secure a sufficient bag-like shape of the lens capsule.

Capsular tension rings and fixation arms of intraocular lenses (haptics) are used in order to secure a round shape of the equatorial region of the lens capsule. Capsular tension rings are used to prevent after-cataracts by preventing proliferation and extension of the epithelial cells of the anterior lens into the posterior capsule and intraocular lenses are used for correcting visual acuity. In cases where the Zinn zonule ruptures, capsular tension rings and intraocular lenses may be dislocated into the vitreous cavity resulting in the possible need for resurgery.

SUMMARY OF THE INVENTION

Accordingly, it is a purpose of the present invention to provide a device and a method to facilitate the retention of a lens during intraocular surgery.

In cataract surgery, retaining the equatorial region of the capsular bag in patients with a brittle or ruptured Zinn zonule is carried out with a pad, using a surgery auxiliary device which allows use of the safe and reliable procedure of phacoemulsification/aspiration.

Moreover, in intraocular lens implantation surgery, a pad is used to secure the equatorial region of the lens capsule in patients with a brittle or ruptured Zinn zonule, and a surgical auxiliary device is used to safely and reliably implant the intraocular lens in the lens capsule.

In cataract/intraocular lens implantation surgery, according to the present invention, in order to retain the equatorial region of the lens capsule in place in patients with a weak or ruptured Zinn zonule, a rod-shaped device made of a synthetic resin or metal is used. The device is equipped with a handle having a length of 6 mm or more, a thickness ranging from 0.01 mm to 1.0 mm, and a tip bent into an acute angle, with the length to this angled tip being 1.5 mm or more. The bent tip has a bendable or deformable linear branched or flat pad, with each linear portion being 0.01-1 mm in thickness, a width or space between the branched lines being 1 mm or more, and the flat pad has a surface area of 1 $mm^2$ or more.

The branched tips of the pad extend in an upward and downward direction, relative to an axis A of the handle, to contact the equatorial region of the lens capsule in an anterior and posterior direction, thereby securing a bag shape. Alternatively, each branch can extend to the right and left, with the right-to-left width or space again being 1 mm or more, with the equatorial region of the lens capsule being spread out via the pad to secure the equator.

Alternatively, in the retaining device for the equatorial region of a lens capsule according to the present invention, the tip of the bend may be flat, and the surface thereof, a spatula-shaped pad, to secure the equatorial region of the lens capsule. This device may be used in cataract or intraocular lens implantation surgery.

An opposite tip of the handle may be in the form of a loop, with said loop being sutured underneath the conjunctiva or in the sclera in order to tie and implant the present device. The loop shape may also be an easy-to-suture hook shape. By means of this retaining device, dislocation into the vitreous cavity of the intraocular lens following intraocular lens implantation is prevented, thus maintaining the postoperative visual acuity of the patient.

The device may be made with a synthetic resin selected from polypropylene, nylon, silicone, polyvinyl chloride, polyvinyl fluoride, polymethyl methacrylate, polyimide, or a shape-memory resin, or a metal selected from stainless steel, aluminum, titanium, a shape-memory metal, etc. Moreover, provided that the material is safe for the human body and surgically effective, other resins or metals/alloys may also be used.

Other features and advantages of the present invention will be apparent from the following description taken in conjunction with the accompanying drawings, in which like reference characters designate the same or similar parts throughout the Figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Figure 1:
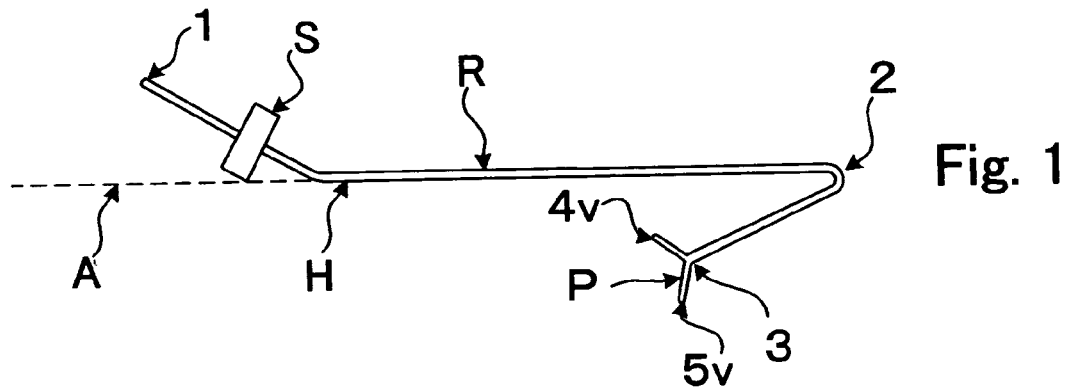
FIG. 1 is a side view of one embodiment of the device for retaining the equatorial region of the lens capsule using a pad including upward and downward branches.

FIG. 1 shows a first embodiment of the device of the present invention. The device R can be used in ophthalmologic surgery as a surgical auxiliary device for cataract patients, particularly in the case of phacoemulsification/aspiration and intraocular lens implantation surgery.

In the following description, various dimensions and materials are described for the purpose of providing examples to better understand the embodiments. However, it is not intended to limit interpretation of the claims thereto.

The length from a first end 1 of a rod-shaped handle H of the device R to an opposite bent portion 2 is approximately 10 mm, and preferably at least 6 mm.

The bend of the bent portion 2 forms an acute angle with a branch 3. The branch 3 includes a tip 4v for the anterior capsule side, and a tip 5v for the posterior capsule side, respectively extending upwardly and downwardly relative to an axis A of the handle H. The length from this bent portion 2 to the branch 3 is approximately 1.5 mm or more, with a preferred maximum length of about 5 mm. The distance from the bent portion 2 to the tip 4v or 5v shown in FIG. 1 is about 2.25 mm.

A pad P is formed by the tips 4v and 5v that is approximately 1.25 mm wide. The device R shown in FIG. 1 is made, e.g., with 5-0 nylon sutures having a thickness of 0.15 mm, and silicone can be used for a positioning stopper S located on the handle H of the device.

Figure 2:
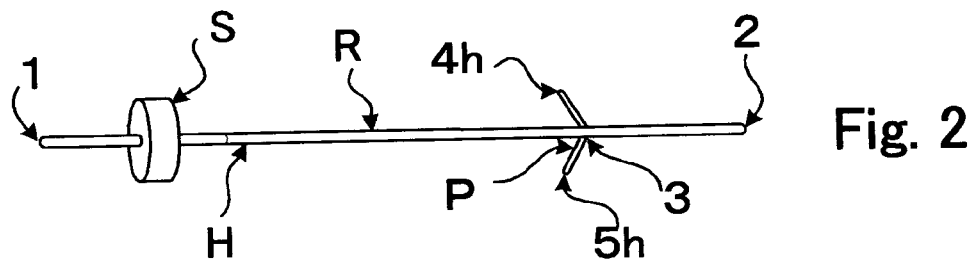
FIG. 2 is a top view of another embodiment of the device for retaining the equatorial region of the lens capsule using a pad including right and left branches.

FIG. 2 is a top view showing an alternate device R having a pad P, but tips 4h and 5h extend to the right and left of the axis A, as opposed to up and down, as shown in FIG. 1. Otherwise, in comparison to the embodiment shown in FIG. 1, both embodiments have an upward bend at the left side of FIGS. 1 and 2, and a downward bend at the opposite end of the device.

On the periphery of the cornea, for example, the device R may be smoothly inserted into the eye at four wound sites measuring about 1 mm in width made for insertion into the eye.

The pad between tips 4v-5v or between tips 4h-5h may be split up to half of its width up to the branch 3 along a length of 0.75 mm of the 5-0 nylon thread of the device R. This pad P width is in the range of 1 mm to 15 mm, and this width secures the equatorial region. The shape is preferably obtained by thermal forming.

Figure 3A:
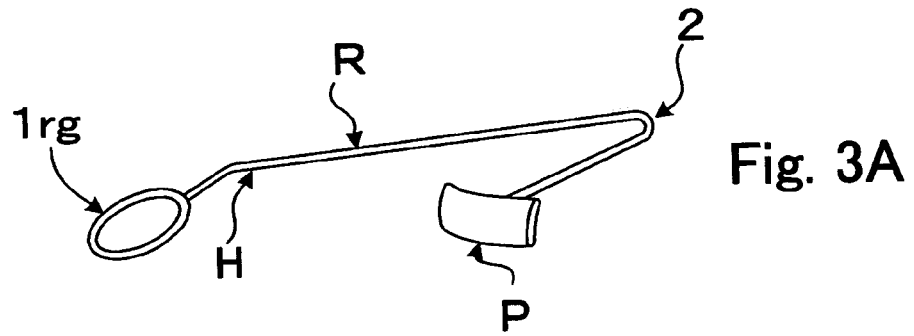
FIG. 3A is a side view of still another embodiment of a device for holding the equatorial region of the lens capsule, having a loop shape at one end that can be sutured, and at the other end, a pad which has a spatula-shape.
Figure 3B:
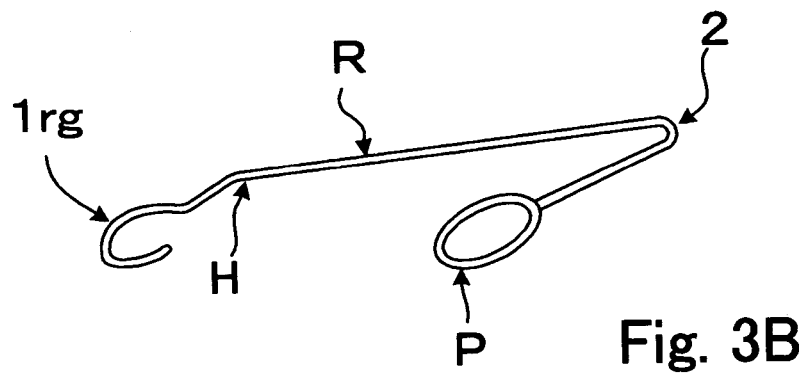
FIG. 3B is a side view of still another embodiment of a device for holding the equatorial region of the lens capsule, having a hook shape at one end that can be sutured, and at the other end, a pad which has a loop shape.

The pad P may also be a spatula-like pad P as shown in FIG. 3A. This spatula pad P may have a contact area with the equatorial region of the capsule ranging from 1 $mm^2$ to 30 $mm^2$, or it may be a loop-type pad, as shown in FIG. 3B. As would be appreciated by one of ordinary skill, the various shapes of the two ends of the device described above can be combined variously as desired for the particular application.

As also shown in FIG. 3A, the first end 1 of the handle H may extend downwardly and be formed, e.g., in a loop lrg, and this loop lrg may be sutured beneath the conjunctiva Ct or sclera Sc. Alternatively, the first end 1 can be configured in other shapes, such as the hook shape shown in FIG. 3B. In this use, in cases of an occurrence of subluxation or luxation of a patient's lens, the concern that the intraocular lens may shift or be dislocated into the vitreous body Vit, thus causing further complications, is eliminated.

The device R, as shown in FIGS. 3A and B, can be used as an auxiliary post-surgical intraocular lens fixation device in cataract patients having a brittle or partially ruptured Zinn zonule. The device R not only prevents further rupturing of the Zinn zonule during cataract/intraocular lens implantation surgery, but it also keeps the position of the implanted intraocular lens as is and helps to stabilize patients' postoperative visual acuity.

Figure 4:
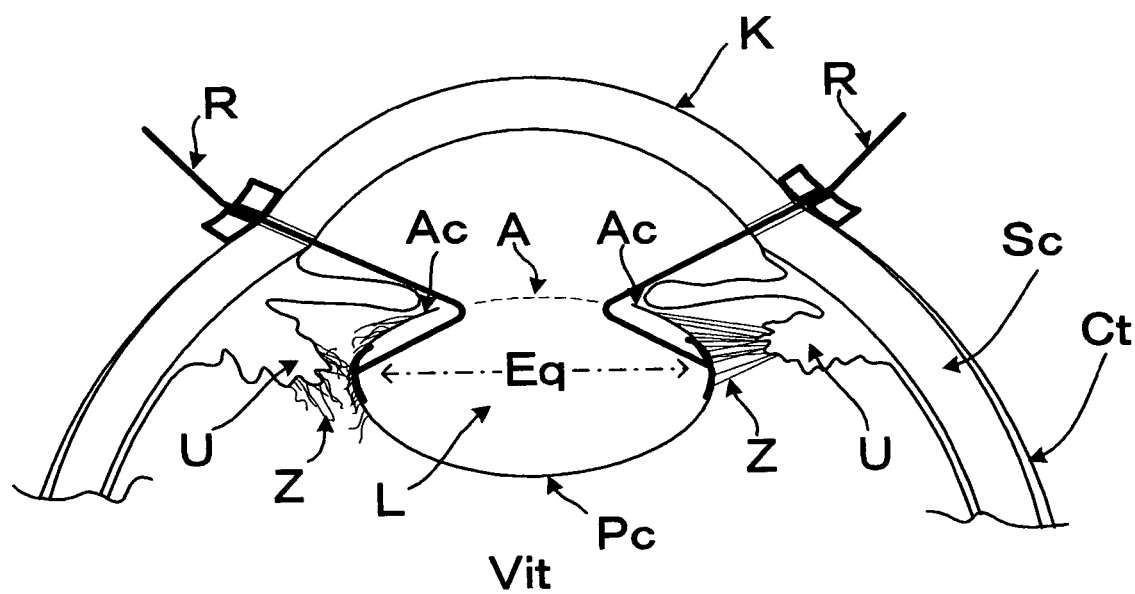
FIG. 4 is a sectional view of the anterior portion of the eyeball in order to illustrate an example of the use of the device shown in FIG. 1.

The device R is used in the eye, as shown in FIG. 4, after carrying out the required preoperative sterilization procedures.

That is, the device R is shown in FIG. 4 during cataract surgery inserted into the lens capsule via puncture wounds on the periphery of the cornea K and a margin of anterior capsulotomy A. More particularly, insertion of the device from the side of the tips 4h and 5h as shown in FIG. 2, or the tip 5v as shown in FIG. 1, into the eye takes place as shown in FIG. 4 from the edge of the cornea K, and insertion into the equatorial region of the eye takes place from the margin of anterior capsulotomy A. In the subsequent phacoemulsification/aspiration surgery, this will aid in emulsification and aspiration of the lens L.

The pad P preferably is softer or more flexible than the rod, so that the tips, e.g., $4v$ and $5v$ can bend relative to the rod in use, as shown in FIG. 4, as they push against the equatorial region of the capsule. That is, the tips should not be stronger or more resilient than the capsule tension. Thus, since the retaining device R has a pad P at the end of the curved rod which fits the inner equator region of the capsule, the pad should be rounded or easily bent in order to retain safely and effectively the capsule.

When the device R is installed at four sites at 90-degree intervals on the periphery of the corneal limbus, even if the Zinn zonule Z is brittle or ruptured, the capsules Ac and Pc will be pushed and spread out in four directions, with the equatorial region Eq being held in place as much as possible, and the depth of the bag will also be preserved. For clarification purposes, FIG. 4 shows a section of the eyeball with the device R inserted from the left and right directions.

With the pad P resting against the equatorial region Eq of the lens capsule of the device R, as shown in FIG. 4, the equatorial region Eq is spread out in three dimensions to the side of the anterior capsule Ac and the side of the posterior capsule Pc, thus facilitating phacoemulsification/aspiration in the patient. Moreover, the subsequent implantation of the intraocular lens in the capsule is also facilitated.

Following anterior capsulotomy A, if the lens nucleus is hard, after separating the lens nucleus and the lens cortex by hydraulic pressure, the device R is inserted into the lens capsule. What this means is that the device R acts to move the pad P that pushes and expands the lens capsules Ac and Pc, thus helping to hold the lens L of the Zinn zonule Z that is brittle or partially ruptured in place during the operation.

As also shown in FIG. 4, after the device R is inserted into the intraocular lens capsule, the pad is applied to the equatorial region Eq inside the eye. On the left side of the Zinn zonule Z, there is a rupture shown from the uvea U, but the Zinn zonule Z on the right side is not ruptured from the uvea U. The device is inserted and installed in this manner, after which phacoemulsification/aspiration is carried out and the intraocular lens is implanted.

Before the device of the present invention is inserted into the eye, the nucleus and cortex are separated by hydraulic pressure in lenses having a hard nucleus. After nuclear separation, when the device of the present invention is installed in the eye, the pads P shown in FIGS. 1 to 3 are in contact with the cortex of the equatorial region of the capsule. At this time, the cortex under the pad is aspirated using a phacoemulsification/aspiration needle, and although the pad of this device vibrates, cortical aspiration is not prevented.

Experiments

Using eyeballs extracted from sacrificed pigs, the device R shown in FIG. 1 was tested. After anterior capsulotomy under a microscope, an area close to a hemisphere was removed from the posterior eye region, the Zinn zonule was cut along half its circumference, and the benefits of the device R were confirmed inside the capsule from the posterior region of the eye.

Four sites on the edge of the cornea were punctured with a width of 1 mm at 90-degree intervals, four of the devices of the present invention were inserted into the mucous lens via a margin of anterior capsulotomy, and the pad P of the present invention was installed toward the equatorial region Eq of the lens, as shown in FIG. 4. The position was then fixed using a positioning stopper S.

At this time, as shown in FIG. 1, the motion of the tips $4v$-$5v$ of the device R from the posterior eye was observed. It was possible to fix the tips in the equatorial region without puncturing the capsule. In this situation, it was possible to carry out phacoemulsification/aspiration and intraocular lens implantation.

The lens capsule of the pig eye is tougher than that of the human eye, but it maintains a bag shape, and it was confirmed that it is possible to safely and reliably carry out cataract surgery/intraocular lens implantation.

The device for retaining the equatorial region of the lens capsule of the present invention may be used as an auxiliary device in surgery conducted in cataract patients having a brittle or partially ruptured Zinn zonule. The device of the present invention prevents further rupturing of the Zinn zonule during cataract/intraocular lens implantation surgery, accurately fixes the position of the intraocular lens, and helps the patient to recover visual acuity.

Using the device of the present invention prevents the surgeon from causing subluxation or luxation of the lens and prevents the further complications of shifting of the lens or intraocular lens and dislocation into the vitreous cavity.

In phacoemulsification/aspiration surgery, if the lens capsule, which is in the form of a bag, becomes unstable, this increases the risk of posterior capsule rupture due to the phacoemulsification/aspiration needle, and for this reason, use of the device of the present invention allows the surgeon to prevent such rupture during phacoemulsification/aspiration surgery, particularly in patients with a brittle or partially ruptured Zinn zonule, thus making it possible to carry out safe surgery without any additional complications.

For example, even with the use of only one site on the equatorial region, the device of the present invention can be used at the insertion site of the phacoemulsification/aspiration needle, thus making it easy for the surgeon to carry out phacoemulsification/aspiration or intraocular lens implantation, even in patients without brittleness or rupture of the Zinn zonule.

The device of the present invention also makes it possible to three-dimensionally secure the equatorial region of the lens capsule in a way that would not be possible with an iris retractor or lens capsule stabilizer like Mackool's discussed above, and phacoemulsification/aspiration or intraocular lens implantation surgery can therefore be carried out easily. Even if the vitreous pressure is somewhat higher than that of the posterior eye, the equatorial region of the capsule can be three-dimensionally secured.

Moreover, as shown in FIGS. 3A and B, the device for retaining the equatorial region of the lens capsule of the present invention may be in a form that can be sutured under the conjunctiva or into the sclera, thus implanting the device in the eye. In such cases, the shape of the pad may be any of the shapes shown in FIGS. 1-3. In this manner, it is possible to prevent dislocation of the intraocular lens into the vitreous cavity following intraocular lens implantation surgery over an extended time period. The surgeon can avoid resurgery and prevent an associated decrease in the patient's visual acuity.

In patients with a brittle or partially ruptured Zinn zonule, the lens may be rendered unstable and moved by the resection needle during anterior capsulotomy. This capsulotomy technique is therefore difficult for the surgeon, and in many cases, either fissures will develop on the margin of the capsulotomy, or it is not possible to make a skillful round opening. However, the device of the present invention can be used even if there are small defects or fissures in the margin of the capsulotomy, as pressure is applied on the equatorial region of the lens capsule rather than the anterior capsule.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

What is claimed is:

1. An ophthalmic device for retaining a lens capsule, comprising:
   a single rod forming a linear handle portion, an end of said rod being bent at an acute angle relative to the linear portion of the handle so that the end is not parallel to the linear portion of the handle, and an extension formed at a free portion of the end,
   wherein the extension is not parallel to the linear portion of the handle,
   wherein the extension includes two linear tips connected to and diverging from the end with respect to each other in opposite directions, and
   wherein each tip has a blunt free terminus.

2. The device according to claim 1, wherein one of the linear tips extends upward to its terminus and the other extends downward to its terminus, each relative to an axis of the linear portion of the handle.

3. The device according to claim 1, wherein one of the linear tips extends leftward to its terminus and rightward to its terminus, each relative to an axis of the linear portion of the handle.

4. The device according to claim 1, wherein the rod includes a second opposite end which is bent relative to the linear portion of the handle and includes thereon a positioning stopper.

5. The device according to claim 1, wherein the device is made of a synthetic resin selected from at least one of polypropylene, nylon, silicone, polyvinyl chloride, polyvinyl fluoride, polymethyl methacrylate, polyimide, and a shape-memory resin.

6. The device according to claim 1, wherein the device is made of a metal selected from at least one of stainless steel, aluminum, titanium, and a shape-memory metal.

7. The device according to claim 1, wherein the extension has a width in the range of about 1 mm to 15 mm.

8. The device according to claim 1, wherein the extension is made of a material that is more flexible than the handle.

* * * * *